(12) United States Patent
Fukumoto et al.

(10) Patent No.: US 10,094,031 B2
(45) Date of Patent: Oct. 9, 2018

(54) METHOD FOR MANUFACTURING REDUCED GLUTATHIONE

(71) Applicant: KYOWA HAKKO BIO CO., LTD., Tokyo (JP)

(72) Inventors: Kenta Fukumoto, Tokyo (JP); Miyuki Fukuda, Tokyo (JP); Mitsutaka Kino, Tokyo (JP)

(73) Assignee: Kyowa Hakko Bio Co., Ltd., Tokyo (JP)

(*) Notice: Subject to any disclaimer, the term of this patent is extended or adjusted under 35 U.S.C. 154(b) by 273 days.

(21) Appl. No.: 14/770,768

(22) PCT Filed: Feb. 28, 2014

(86) PCT No.: PCT/JP2014/055053
§ 371 (c)(1),
(2) Date: Aug. 26, 2015

(87) PCT Pub. No.: WO2014/133129
PCT Pub. Date: Sep. 4, 2014

(65) Prior Publication Data
US 2016/0002797 A1   Jan. 7, 2016

(30) Foreign Application Priority Data
Feb. 28, 2013 (JP) ................. 2013-038890

(51) Int. Cl.
*C30B 7/00* (2006.01)
*C25B 3/00* (2006.01)
(Continued)

(52) U.S. Cl.
CPC .............. *C25B 3/04* (2013.01); *C07K 5/0215* (2013.01); *C25B 9/08* (2013.01)

(58) Field of Classification Search
USPC ............................................ 205/435; 117/68
See application file for complete search history.

(56) References Cited

U.S. PATENT DOCUMENTS

| | | | |
|---|---|---|---|
| 5,395,488 A | 3/1995 | Scharbert et al. | |
| 2012/0118756 A1 | 5/2012 | Fukumoto | |
| 2014/0027302 A1* | 1/2014 | Fukumoto | C07K 5/0215 205/437 |

FOREIGN PATENT DOCUMENTS

| | | |
|---|---|---|
| CA | 869067 A | 4/1971 |
| CN | 102803567 A | 11/2012 |

(Continued)

OTHER PUBLICATIONS

Dohan et al., "Electrolytic Reduction and Determination of Oxidized Glutathione," Biochemical Research Foundation (Sep. 1939), pp. 403-407. (Year: 1939).*

(Continued)

*Primary Examiner* — Edna Wong
(74) *Attorney, Agent, or Firm* — Leydig, Voit & Mayer, Ltd.

(57) ABSTRACT

A method of producing reduced glutathione by electrolytic reduction of oxidized glutathione using a cathode cell and an anode cell separated from each other by a separating membrane, including using a cathode having a metal cathode surface, and, as a cathode solution, an aqueous oxidized glutathione solution having a pH adjusted to higher than 3.0 and 5.0 or below by adding a base, which is added with the same metal as the metal of the cathode surface, a metal salt thereof, or a metal oxide thereof.

16 Claims, 2 Drawing Sheets

(51) Int. Cl.
C25B 3/04 (2006.01)
C07K 5/02 (2006.01)
C25B 9/08 (2006.01)

(56) References Cited

FOREIGN PATENT DOCUMENTS

| | | | | | |
|---|---|---|---|---|---|
| JP | 52131528 | A | * 11/1977 | ........... | C07C 103/52 |
| JP | S52-131527 | A | 11/1977 | | |
| JP | S52-131528 | A | 11/1977 | | |
| JP | H06-057471 | A | 3/1994 | | |
| WO | WO 2010/140625 | A1 | 12/2010 | | |
| WO | WO 2012/137824 | A1 | 10/2012 | | |
| WO | WO-2012137824 | A1 | * 10/2012 | ........... | C07K 5/0215 |

OTHER PUBLICATIONS

Shapoval et al., "Electrochemical Simulation of Redox Reactions of Glutathione," Russian Journal of General Chemistry (no month, 2008), vol. 78, No. 12, pp. 2386-2390. (Year: 2008).*

Japanese Patent Office, International Search Report in International Patent Application No. PCT/JP2014/055053 (dated May 27, 2014).

\* cited by examiner

METHOD FOR MANUFACTURING REDUCED GLUTATHIONE

CROSS-REFERENCE TO RELATED APPLICATIONS

This patent application is the U.S. national phase of International Patent Application No. PCT/JP2014/055053, filed Feb. 28, 2014, which claims the benefit of Japanese Patent Application No. 2013-038890, filed on Feb. 28, 2013, which are incorporated by reference in their entireties herein.

TECHNICAL FIELD

The present invention relates to a method of producing reduced glutathione by electrolytic reduction of oxidized glutathione.

BACKGROUND ART

As a method of producing reduced glutathione by electrolytic reduction of oxidized glutathione, a method using an aqueous oxidized glutathione solution acidified by adding a mineral acid such as concentrated hydrochloric acid and the like to a cathode side electrolytic cell (patent document 1), a method using an aqueous oxidized glutathione solution having electrical conductivity improved by adding a conducting agent other than an acid for an electrolytic cell on the cathode side (patent document 2), and a method using an aqueous oxidized glutathione solution having a pH adjusted to higher than 3.0 and 7.0 or below by adding a base, as an electrolytic cell on the cathode side (patent document 3) are known.

However, since the methods of patent documents 1 and 2 include electrolytic reduction in an acidic region, when a metal is used as the cathode, corrosion of the metal of the cathode was unavoidable.

While patent document 3 teaches that corrosion of the metal of the cathode can be suppressed since electrolytic reduction in a neutral region is possible, complete prevention of corrosion of the metal of the cathode has not been achieved.

DOCUMENT LIST

Patent Documents patent document 1: JP-A-52-131528
patent document 2: WO 2010/140625
patent document 3: WO 2012/137824

SUMMARY OF THE INVENTION

Problems to be Solved by the Invention

As a method of producing reduced, glutathione by electrolytic reduction of oxidized glutathione, a method of efficient electrolytic reduction while preventing corrosion of the metal of the cathode has been demanded.

Means of Solving the Problems

The present invention relates to the following (1)-(7).
(1) A method of producing reduced glutathione by electrolytic reduction of oxidized glutathione using a cathode cell and an anode cell separated from each other by a separating membrane, comprising using a cathode having a metal cathode surface, and, as a cathode solution, an aqueous oxidized glutathione solution having a pH adjusted to higher than 3.0 and 5.0 or below by adding a base, which is added with the same metal as the metal of the cathode surface, a metal salt thereof, or a metal oxide thereof.
(2) The production method of the above-mentioned (1), wherein the metal on the cathode surface is a metal showing high hydrogen overvoltage.
(3) The production method of the above-mentioned (1) or (2), wherein the base is hydroxide, carbonate or hydrogencarbonate of sodium or potassium.
(4) The production method of any one of the above-mentioned (1) to (3), wherein the aqueous oxidized glutathione solution has a concentration of not less than 20 g/L.
(5) The production method of any one of the above-mentioned (1) to (4), wherein the same metal as the metal of the cathode surface, a metal salt thereof, or a metal oxide thereof has a concentration after addition of 0.5-50 mmol/L.
(6) The production method of any one of the above-mentioned (1) to (5), wherein the electrolytic reduction is performed at an electric current density of 0.1-30 $A/dm^2$.
(7) A method of producing a reduced glutathione crystal, comprising subjecting a reduced glutathione solution, produced by the production method of any one of the above-mentioned (1) to (6), to 1) adjustment of pH, or 2) removal of cation by passing the solution through an ion exchange column, followed by crystallization.

Effect of the Invention

According to the present invention, reduced glutathione can be efficiently produced while preventing corrosion of the metal of the cathode, by electrolytic reduction of oxidized glutathione.

DESCRIPTION OF EMBODIMENTS

Figure 1:
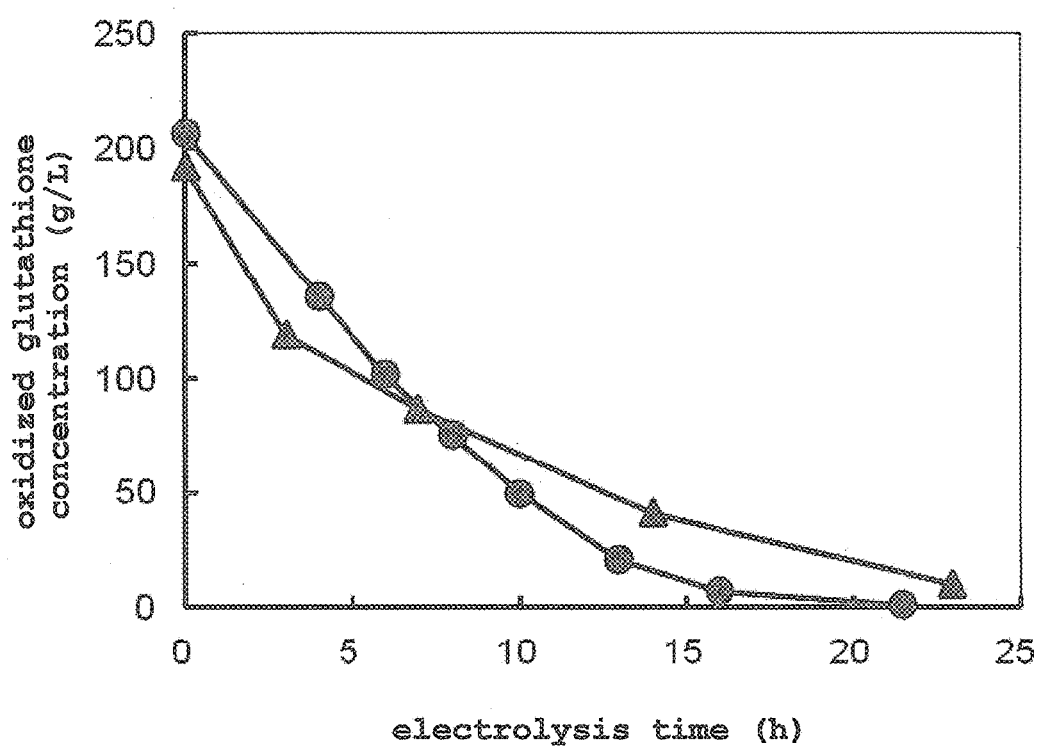
FIG. 1 shows the relationship between the oxidized glutathione concentration and electrolysis time when electrolytic reduction of oxidized glutathione is performed using a galvanized stainless steel electrode or zinc electrode as the cathode, wherein the vertical axis shows the concentration of oxidized glutathione in a cathode solution (g/L) and the horizontal axis shows an electrolytic reduction time (h).

The method of the present invention is, a method of producing reduced glutathione by electrolytic reduction of oxidized glutathione using a cathode cell and an anode cell separated from each other by a separating membrane, comprising using a cathode having a metal cathode surface, and, as a cathode solution, an aqueous oxidized glutathione solution having a pH adjusted to higher than 3.0 and 5.0 or below by adding a base, which is added with the same metal as the metal of the cathode surface, a metal salt thereof, or a metal oxide thereof.

A metal to be used for the above-mentioned cathode is not particularly limited as long as the cathode surface is a metal and the metal can electrolytically reduce oxidized glutathione. Preferred is a metal having a high hydrogen overvoltage. Examples of such metal include zinc, lead, copper, nickel and silver, preferably zinc, silver and lead, more preferably zinc and lead, most preferably zinc.

The above-mentioned cathode may also be a cathode wherein a metal plated layer suitable for electrolytic reduction of oxidized glutathione is formed on the surface of an electrode base material.

The electrode base material is not limited as long as it can electrolytically reduce oxidized glutathione by forming the below-mentioned metal plated layer. Examples thereof include iron, stainless steel, copper, aluminum, and an alloy using these, and oxide of these metals or alloy, preferably iron and stainless steel, more preferably stainless steel.

The electrode base material may also be a material other than the above-mentioned metals, as long as it is superior in conductiveness and corrosion resistance, such as carbon materials such as graphite, graphite, fiber carbon and the like or a conductive polymer.

A metal used for a plated layer is not particularly limited as long as it permits electrolytic reduction of oxidized glutathione. Preferable examples thereof include metals having high hydrogen overvoltage. Examples of such metal include zinc, lead, copper, nickel, and silver, preferably zinc, silver and lead, more preferably zinc and lead, most preferably zinc.

As the above-mentioned cathode solution, an aqueous oxidized glutathione solution having a pH adjusted by adding a base to preferably higher than 3.0 and not more than 5.0, more preferably higher than 3.0 and not more than 4.75 is used.

Examples of the base include bases capable of neutralizing an aqueous oxidized glutathione solution, preferably bases containing alkali metal ions such as sodium, potassium and the like, alkaline earth metal ions such as calcium and the like, ammonium ion, imidazolium ion, and phosphonium ion, more preferably bases containing alkali metal ion, particularly preferably bases containing a cation of sodium and potassium. The aforementioned base containing cation may have any form such as forms of hydroxide, carbonate, hydrogencarbonate and the like, and the method of adjusting pH is not limited and pH can be adjusted by a known method.

While the concentration of the aqueous oxidized glutathione solution is not limited, it is 20 g/L or more, preferably 100 g/L or more, more preferably 200 g/L or more, further preferably 300 g/L or more, most preferably 400 g/L or more. The higher the concentration of oxidized glutathione in the cathode cell becomes, the more improved the conductivity is to enable smooth supply of oxidized glutathione to a surface of the electrode. As a result, the efficiency of electrolytic reduction is increased.

The saturated solubility of oxidized glutathione at the isoelectric point in water at ambient temperature (25° C.) is not more than 20 g/L. It is known that the solubility becomes high at a pH higher than the isoelectric point (patent document 3). Therefore, when an aqueous oxidized glutathione solution has a pH higher than 3.0 and not more than 5.0, which pH is higher than the isoelectric point, an aqueous oxidized glutathione solution at not less than 20 g/L can be prepared.

The above-mentioned cathode solution is added with the same metal as the metal of the cathode surface, a metal salt thereof, or a metal oxide thereof. As a result, when oxidized glutathione is electrolytically reduced under the aforementioned conditions, electrocrystallization of the metal on the cathode surface occurs simultaneously with the electrolytic reduction, and corrosion of the electrode can be prevented. That is, electrolytic reduction of oxidized glutathione can be performed industrially continuously, without exchanging the electrode of the cathode or by reducing the exchange frequency thereof.

Examples of the same metal salt as the metal of the cathode surface include hydrochloride, sulfate, sulfonate, nitrate, bromate, carboxylate, hydroxide and the like, preferably hydrochloride, sulfate and the like.

The concentration of the same metal as the metal of the cathode surface, a metal salt thereof, or a metal oxide thereof to be added is not limited as long as electrocrystallization occurs under the aforementioned conditions of electrolytic reduction. For example, the concentration after addition is 0.5-50 mmol/L, preferably 1-30 mmol/L, most preferably 1-10 mmol/L. When the additives are not immediately dissolved in a cathode solution, they are added to the above-mentioned concentration assuming that they will be completely dissolved along with the progress of the electrolytic reduction.

Examples of a method of adding the same metal as the metal of the cathode surface, a metal salt thereof, or a metal oxide thereof include a method including addition before the start of electrolytic reduction, a method including gradual addition during electrolytic reduction and the like. When the additives are not immediately dissolved in a cathode solution, for example, the additives in the form of a powder may be added.

As the above-mentioned anode, any metal can be used as long it is an insoluble metal. A metal superior in the corrosion resistance is preferable. Examples thereof include platinum plated titanium, platinum-iridium, lead, lead alloy, lead dioxide, gold, and titanium oxide, preferably platinum plated titanium.

The above-mentioned solution for an anode cell is not particularly limited as long as it is a conductive aqueous solution, and inorganic acid solutions such as hydrochloric acid and sulfuric acid, organic acid solutions such as acetic acid and propionic acid, a solution dissolving a conducting agent other than acid and the like can be mentioned. As for the concentration of inorganic acid or organic acid, conductivity is low at low concentrations, and ion exchange membrane is easily deteriorated at high concentrations. Therefore, the concentration thereof to be used is 0.5-3 mol/L, preferably 1-2 mol/L.

As the above-mentioned separating membrane, any membrane can be used as long as it can reduce leakage of reduced glutathione produced in the cathode cell into the anode cell. Preferred is an ion exchange membrane, more preferred is a cation exchange membrane, specifically SELEMION CMT (manufactured by Asahi Glass Company) or Nafion (manufactured by DuPont).

In the method of the present invention, electric current density, voltage, temperature and the like are not particularly limited. As conditions for improving reduction efficiency while suppressing decomposition of the produced reduced glutathione, the electric current density is preferably 0.1-30 A/dm$^2$, more preferably 1-20 A/dm$^2$, further preferably 5-15 A/dm$^2$, the voltage is preferably 1-20 V, more preferably 2-15 V, further preferably 3-10 V, and the temperature is preferably 4-50° C., more preferably 10-30° C., further preferably 10-25° C.

After completion of electrolytic reduction, a cathode solution which contains the produced reduced glutathione can be directly used for crystallization by adjusting pH to near the isoelectric point of reduced glutathione (pH 3.0) with various mineral acids such as sulfuric acid and hydrochloric acid. In addition, the cathode solution containing reduced glutathione is desalted by passing through an ion exchange column, and the aqueous desalted reduced glutathione solution may be directly used for crystallization. Examples of the ion exchange resin include strongly acidic cation exchange resins represented by SK-116 and SK-104 (both DIAIONs, manufactured by Mitsubishi Chemical Corporation), and weakly basic ion exchange resins represented by WA-30 and WA-21 (both DIAIONs, manufactured by Mitsubishi Chemical Corporation). The pH-adjusted or desalted reduced glutathione can be crystallized by concentration, appropriate addition of a solvent or seed crystal, and cooling.

REFERENCE EXAMPLE

In the Example and Comparative Example of the present invention, the concentrations of oxidized glutathione and reduced glutathione were quantified under the following HPLC conditions.
HPLC Conditions
column: Inertsil ODS-3 φ3×100 mm
column temperature: 35° C.
buffer: 3% methanol solution containing 0.2% sodium 1-heptanesulfonate, 6.8% potassium dihydrogen phosphate (adjusted to pH 3.0 with phosphoric acid)
flow rate: 0.5 mL/min
detector: UV detector (wavelength 210 nm)
Examples of the present invention are shown below; however, the present invention is not limited by the Examples.

Example 1

Electrolytic Reduction of Oxidized Glutathione by Using Galvanized Stainless Steel Electrode Sodium hydroxide was added to an aqueous oxidized glutathione solution to allow pH to be adjusted to 4.0, whereby aqueous oxidized glutathione solution was prepared. Powder zinc was added to 160 mg/L, whereby 200 g/L aqueous oxidized glutathione solution was prepared. As the electrolytic cell, anode cell (15 L) and cathode cell (15 L) were used, and the both were separated by a cation exchange membrane SELEMION CMT (manufactured by Asahi Glass Company) with an effective membrane area of 1.8 $dm^2$. Iridium oxide-coated titanium was used as the anode, and galvanized stainless steel (SUS316) was used as the cathode. The distance between the electrode and the cation exchange membrane was set to 1.9 mm, and the circulation flow was set to 240 L/h. The anode cell contained 0.50 mol/L sulfuric acid solution (10 L), and the cathode cell contained the aqueous oxidized glutathione solution (200 g/L, 10 L) prepared above.

Electrolytic reduction reaction was performed at electrolytic voltage 5-7V, electric current density 10 A/$dm^2$, and room temperature. The resultant product in the cathode cell was quantified by HPLC under the conditions described in Reference Example, and production of 1.99 kg of reduced glutathione in 21.5 hr was found, which was confirmed to be a reduction rate equal to or not less than that of Comparative Example 1 (conversion ratio 99.5%).

The amount of zinc ion in the cathode solution after the completion of electrolysis was confirmed by Zeeman atomic absorption spectrophotometer (Z-2310 manufactured by Hitachi High-Technologies Corporation). It was confirmed that zinc concentration on completion of the electrolytic reduction was 8 mg/L, and that electrocrystallization of zinc occurred along with the electrolytic reduction.

Comparative Example 1

Electrolytic Reduction of Oxidized Glutathione by Using Zinc Electrode

Sodium hydroxide was added to an aqueous oxidized glutathione solution to allow pH to be adjusted to 6.5, whereby aqueous oxidized glutathione solution was prepared, whereby 200 g/L aqueous oxidized glutathione solution was prepared. As the electrolytic cell, anode cell (15 L) and cathode cell (15 L) were used, and the both were separated by a cation exchange membrane SELEMION CMT (manufactured by Asahi Glass Company) with an effective membrane area of 1.8 $dm^2$. Iridium oxide-coated titanium was used as the anode, and zinc electrode was used as the cathode. The distance between the electrode and the cation exchange membrane was set to 1.9 mm, and the circulation flow was set to 240 L/h. The anode cell contained 0.50 mol/L sulfuric acid solution (10 L), and the cathode cell contained the aqueous oxidized glutathione solution (200 g/L, 10 L) prepared above.

Electrolytic reduction reaction was performed at electrolytic voltage 5-7V, electric current density 10 A/$dm^2$, and room temperature. The resultant product in the cathode cell was quantified by HPLC under the same conditions as in Reference Example, and production of 1.88 kg of reduced glutathione in 23 hr was confirmed (conversion ratio 94.2%). The amount of zinc ion in the cathode solution after the completion of electrolysis was confirmed by Zeeman atomic absorption spectrophotometer (Z-2310 manufactured by Hitachi High-Technologies Corporation). It was confirmed that zinc concentration on completion of the electrolytic reduction was 67 mg/L, and that zinc eluted from the cathode during the electrolytic reduction.

INDUSTRIAL APPLICABILITY

According to the method of the present invention, reduced glutathione can be efficiently produced while preventing corrosion of the metal of the cathode, by electrolytic reduction of oxidized glutathione.

EXPLANATION OF SYMBOLS

In FIG. 1, ● shows concentration change of oxidized glutathione in electrolytic reduction of oxidized glutathione by using a galvanized stainless steel electrode at a cathode solution pH 4.0 (Example), and ▲ shows concentration change of oxidized glutathione in electrolytic reduction of oxidized glutathione by using a zinc electrode at a cathode solution pH 6.5 (Comparative Example).

Figure 2:
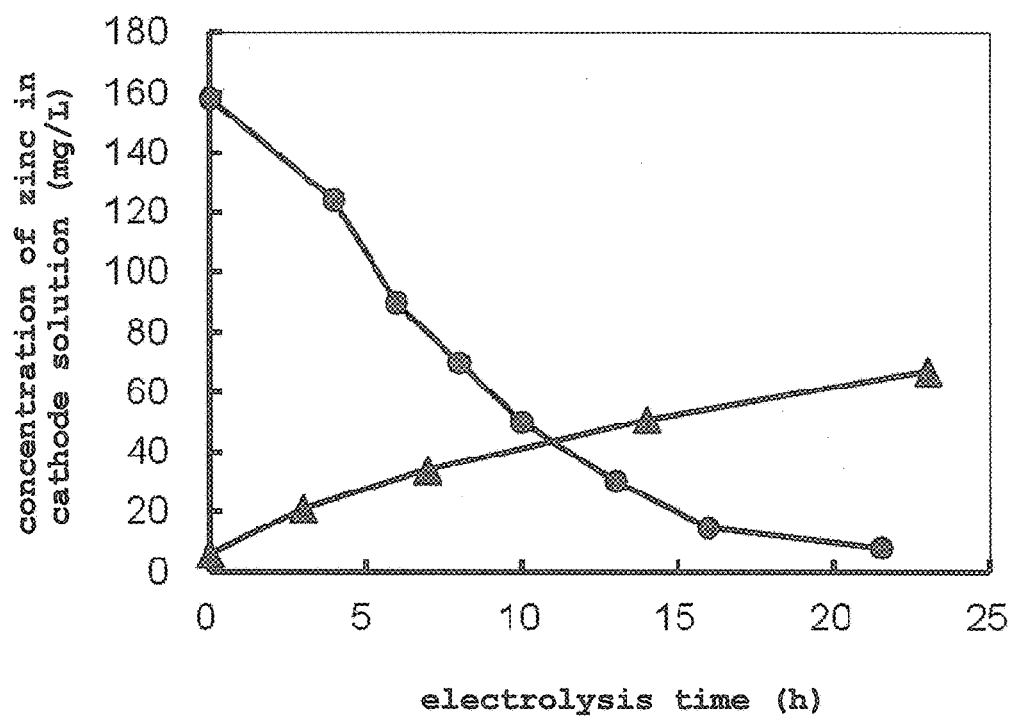
FIG. 2 shows the concentration of zinc in the cathode solution during electrolytic reduction of oxidized glutathione by using a galvanized stainless steel electrode or zinc electrode as the cathode, wherein the vertical axis shows the concentration (mg/L) of zinc in the cathode solution, and the horizontal axis shows an electrolytic reduction time (h).

In FIG. 2, ● shows concentration of zinc in cathode solution in electrolytic reduction of oxidized glutathione by using a galvanized stainless steel electrode at a cathode solution pH 4.0 (Example), and ▲ shows concentration of zinc in cathode solution in electrolytic reduction of oxidized glutathione by using a zinc electrode at a cathode solution pH 6.5 (Comparative Example).

The invention claimed is:
1. A method of producing reduced glutathione comprising electrolytically reducing oxidized glutathione in a cathode solution to produce reduced glutathione in a system comprising

(a) a cathode cell comprising a cathode having a metal cathode surface, wherein the metal on the cathode surface is a metal showing high hydrogen overvoltage,
(b) an anode cell comprising an anode,
(c) a membrane separating the cathode cell and the anode cell, and
(d) the cathode solution that is an aqueous oxidized glutathione solution comprising, dissolved therein, a metal-containing compound, a metal salt, or a metal oxide,
wherein the metal of the metal-containing compound, the metal salt, or the metal oxide is the same metal as the metal of the cathode surface, and
wherein the aqueous oxidized glutathione solution has a pH adjusted to be higher than 3.0 and up to 5.0 by adding a base thereto.

2. The production method according to claim 1, wherein the base is hydroxide, carbonate or hydrogen carbonate of sodium or potassium.

3. The production method according to claim 2, wherein the cathode solution comprises oxidized glutathione at a concentration of not less than 20 g/L.

4. The production method according to claim 3, wherein the cathode solution comprises the metal-containing compound, metal salt, or metal oxide at a concentration of 0.5-50 mmol/L.

5. The production method according to claim 4, wherein the electrolytic reduction is performed at an electric current density of 0.1-30 A/dm$^2$.

6. The production method according to claim 4, wherein the metal showing high hydrogen overvoltage is zinc, lead, copper, nickel, or silver.

7. The production method according to claim 1, wherein the cathode solution comprises oxidized glutathione at a concentration of not less than 20 g/L.

8. The production method according to claim 1, wherein the cathode solution comprises the metal-containing compound, metal salt, or metal oxide at a concentration of 0.5-50 mmol/L.

9. The production method according to claim 1, wherein the electrolytic reduction is performed at an electric current density of 0.1-30 A/dm$^2$.

10. The production method according to claim 1, wherein the metal showing high hydrogen overvoltage is zinc, lead, copper, nickel, or silver.

11. A method of producing a reduced glutathione crystal, comprising
electrolytically reducing oxidized glutathione in a cathode solution to produce reduced glutathione in a system comprising
(a) a cathode cell comprising a cathode having a metal cathode surface, wherein the metal on the cathode surface is a metal showing high hydrogen overvoltage,
(b) an anode cell comprising an anode,
(c) a membrane separating the cathode cell and the anode cell, and
(d) the cathode solution that is an aqueous oxidized glutathione solution comprising, dissolved therein, a metal-containing compound, a metal salt, or a metal oxide,
wherein the metal of the metal-containing compound, the metal salt, or the metal oxide is the same metal as the metal of the cathode surface, and
wherein the aqueous oxidized glutathione solution has a pH adjusted to be higher than 3.0 and up to 5.0 by adding a base thereto,
then subjecting the cathode solution comprising reduced glutathione to 1) adjustment of pH, or 2) removal of cation by passing the cathode solution through an ion exchange column, and
then crystallizing the reduced glutathione from the cathode solution to provide a reduced glutathione crystal.

12. A method of producing a reduced glutathione crystal, comprising
electrolytically reducing oxidized glutathione in a cathode solution to produce reduced glutathione in a system comprising
(a) a cathode cell comprising a cathode having a metal cathode surface, wherein the metal on the cathode surface is a metal showing high hydrogen overvoltage,
(b) an anode cell comprising an anode,
(c) a membrane separating the cathode cell and the anode cell, and
(d) the cathode solution that is an aqueous oxidized glutathione solution comprising, dissolved therein, a metal-containing compound, a metal salt, or a metal oxide,
wherein the metal of the metal-containing compound, the metal salt, or the metal oxide is the same metal as the metal of the cathode surface, and
wherein the aqueous oxidized glutathione solution has a pH adjusted to be higher than 3.0 and up to 5.0 by adding a base thereto selected from sodium or potassium hydroxide, sodium or potassium carbonate, and sodium or potassium hydrogen carbonate,
then subjecting the cathode solution comprising reduced glutathione to 1) adjustment of pH, or 2) removal of cation by passing the cathode solution through an ion exchange column, and
then crystallizing the reduced glutathione from the cathode solution to provide a reduced glutathione crystal.

13. A method of producing a reduced glutathione crystal, comprising
electrolytically reducing oxidized glutathione in a cathode solution to produce reduced glutathione in a system comprising
(a) a cathode cell comprising a cathode having a metal cathode surface, wherein the metal on the cathode surface is a metal showing high hydrogen overvoltage,
(b) an anode cell comprising an anode,
(c) a membrane separating the cathode cell and the anode cell, and
(d) the cathode solution that is an aqueous oxidized glutathione solution comprising, dissolved therein, a metal-containing compound, a metal salt, or a metal oxide,
wherein the cathode solution comprises oxidized glutathione at a concentration of not less than 20 g/L,
wherein the metal of the metal-containing compound, the metal salt, or the metal oxide is the same metal as the metal of the cathode surface, and
wherein the aqueous oxidized glutathione solution has a pH adjusted to be higher than 3.0 and up to 5.0 by adding a base thereto,
then subjecting the cathode solution comprising reduced glutathione to 1) adjustment of pH, or 2) removal of cation by passing the cathode solution through an ion exchange column, and
then crystallizing the reduced glutathione from the cathode solution to provide a reduced glutathione crystal.

14. A method of producing a reduced glutathione crystal, comprising
   electrolytically reducing oxidized glutathione in a cathode solution to produce reduced glutathione in a system comprising
      (a) a cathode cell comprising a cathode having a metal cathode surface, wherein the metal on the cathode surface is a metal showing high hydrogen overvoltage,
      (b) an anode cell comprising an anode,
      (c) a membrane separating the cathode cell and the anode cell, and
      (d) the cathode solution that is an aqueous oxidized glutathione solution comprising, dissolved therein, at a concentration of 0.5-50 mmol/L, one of a metal-containing compound, a metal salt, or a metal oxide,
      wherein the metal of the metal-containing compound, the metal salt, or the metal oxide is the same metal as the metal of the cathode surface, and
      wherein the aqueous oxidized glutathione solution has a pH adjusted to be higher than 3.0 and up to 5.0 by adding a base thereto,
   then subjecting the cathode solution comprising reduced glutathione to 1) adjustment of pH, or 2) removal of cation by passing the cathode solution through an ion exchange column, and
   then crystallizing the reduced glutathione from the cathode solution to provide a reduced glutathione crystal.

15. A method of producing a reduced glutathione crystal, comprising
   electrolytically reducing oxidized glutathione in a cathode solution to produce reduced glutathione in a system comprising
      (a) a cathode cell comprising a cathode having a metal cathode surface, wherein the metal on the cathode surface is a metal showing high hydrogen overvoltage,
      (b) an anode cell comprising an anode,
      (c) a membrane separating the cathode cell and the anode cell, and
      (d) the cathode solution that is an aqueous oxidized glutathione solution comprising, dissolved therein, a metal-containing compound, a metal salt, or a metal oxide,
      wherein the metal of the metal-containing compound, the metal salt, or the metal oxide is the same metal as the metal of the cathode surface,
      wherein the aqueous oxidized glutathione solution has a pH adjusted to be higher than 3.0 and up to 5.0 by adding a base thereto, and
      wherein the electrolytic reduction is performed at an electric current density of 0.1-30 A/dm$^2$,
   then subjecting the cathode solution comprising reduced glutathione to 1) adjustment of pH, or 2) removal of cation by passing the cathode solution through an ion exchange column, and
   then crystallizing the reduced glutathione from the cathode solution to provide a reduced glutathione crystal.

16. A method of producing a reduced glutathione crystal, comprising
   electrolytically reducing oxidized glutathione in a cathode solution to produce reduced glutathione in a system comprising
      (a) a cathode cell comprising a cathode having a metal cathode surface, wherein the metal on the cathode surface is a metal showing high hydrogen overvoltage,
      (b) an anode cell comprising an anode,
      (c) a membrane separating the cathode cell and the anode cell, and
      (d) the cathode solution that is an aqueous oxidized glutathione solution comprising, dissolved therein, a metal-containing compound, a metal salt, or a metal oxide,
      wherein the cathode solution comprises oxidized glutathione at a concentration of not less than 20 g/L,
      wherein the cathode solution comprises the metal-containing compound, metal salt, or metal oxide at a concentration of 0.5-50 mmol/L,
      wherein the metal of the metal-containing compound, the metal salt, or the metal oxide is the same metal as the metal of the cathode surface,
      wherein the aqueous oxidized glutathione solution has a pH adjusted to be higher than 3.0 and up to 5.0 by adding a base thereto,
      wherein the base is hydroxide, carbonate or hydrogen carbonate of sodium or potassium,
      wherein the electrolytic reduction is performed at an electric current density of 0.1-30 A/dm$^2$,
   then subjecting the cathode solution comprising reduced glutathione to 1) adjustment of pH, or 2) removal of cation by passing the cathode solution through an ion exchange column, and
   then crystallizing the reduced glutathione from the cathode solution to provide a reduced glutathione crystal.

* * * * *